US006642275B2

(12) United States Patent
Alfonso et al.

(10) Patent No.: US 6,642,275 B2
(45) Date of Patent: Nov. 4, 2003

(54) FORMULATION FOR RESPIRATORY TRACT ADMINISTRATION

(75) Inventors: Mark Alfonso, Easton, CT (US); Paul Goldenheim, Wilton, CT (US); Richard Sackler, Greenwich, CT (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/930,927

(22) Filed: Aug. 16, 2001

(65) Prior Publication Data

US 2002/0022663 A1 Feb. 21, 2002

Related U.S. Application Data

(63) Continuation of application No. 09/435,009, filed on Nov. 5, 1999, now abandoned, which is a continuation of application No. 08/557,279, filed on Nov. 14, 1995, now Pat. No. 6,017,963.

(51) Int. Cl.$^7$ ........................... A01N 33/02; A61F 13/01
(52) U.S. Cl. ....................................... 514/646; 424/434
(58) Field of Search ........................... 514/646; 424/434

(56) References Cited

U.S. PATENT DOCUMENTS

| 3,652,589 A | 3/1972 | Flick et al. ............... 260/326.5 |
| 4,440,777 A | 4/1984 | Zupan ........................ 424/274 |
| 4,464,378 A | 8/1984 | Hussain ..................... 424/260 |
| 4,624,965 A | 11/1986 | Wenig ........................ 514/619 |
| 4,729,997 A | 3/1988 | Wenig ........................ 514/261 |
| 4,749,700 A | 6/1988 | Wenig ...................... 514/225.2 |
| 4,778,810 A | 10/1988 | Wenig et al. ................ 514/263 |
| 4,880,813 A | 11/1989 | Frost ........................... 514/282 |
| 4,973,596 A | 11/1990 | Cohen ......................... 514/354 |
| 5,066,648 A | 11/1991 | Alexander et al. ........... 514/174 |
| 5,204,119 A | 4/1993 | Shiobara et al. ............. 424/489 |
| 5,223,541 A | 6/1993 | Maryanoff et al. ........... 514/644 |
| 5,336,691 A | 8/1994 | Raffa et al. .................. 514/629 |
| 5,446,070 A | 8/1995 | Mantelle ..................... 514/781 |
| 5,451,408 A | 9/1995 | Mezei et al. ................. 424/450 |
| 5,468,744 A | 11/1995 | Raffa et al. .................. 514/282 |
| 5,516,803 A | 5/1996 | Raffa .......................... 514/570 |
| 5,629,011 A | 5/1997 | Illum .......................... 424/434 |

FOREIGN PATENT DOCUMENTS

| DE | 3602370 | 8/1987 | |
| DE | 4221256 | 1/1994 | .......... A61K/9/127 |
| EP | 0189861 | 8/1986 | .......... A61K/47/00 |
| JP | 6199701 | 7/1994 | |
| WO | WO 9304675 | 3/1993 | .......... A61K/31/16 |
| WO | WO93157379 | 8/1993 | .......... A61K/31/485 |
| WO | WO94041339 | 3/1994 | .......... A61K/9/00 |
| WO | WO9410987 | 5/1994 | ............. A61K/9/70 |
| WO | WO94224459 | 10/1994 | .......... A61K/31/48 |

OTHER PUBLICATIONS

Chemical Abstracts AN: 108:82103, Chrubasik et al., "Analgesic use by inhalation", corresponds to DE 3602370 A1, Aug. 6, 1987.

*Remington's Pharmaceutical Sciences*, p. 1451, 1986.

*Primary Examiner*—Padmashri Ponnaluri
(74) *Attorney, Agent, or Firm*—Davidson, Davidson & Kappel, LLC

(57) ABSTRACT

A dosage form for intranasal and/or inhalation administration of an analgesic having low opioid receptor binding activity to a warm blooded animal, that includes a pharmaceutically effective amount of the analgesic. A preferred analgesic is tramadol, a tramadol and/or a pharmaceutically acceptable salt, metabolite or derivative thereof. Methods of making and using the formulation according to the invention are also provided.

12 Claims, No Drawings

FORMULATION FOR RESPIRATORY TRACT ADMINISTRATION

This application is a continuation of U.S. Ser. No. 09/435,009 filed on Nov. 5, 1999, now abandoned which is a continuation of U.S. Ser. No. 08/557,279 filed on Nov. 14, 1995, now U.S. Pat. No. 6,017,963.

FIELD OF THE INVENTION

The present invention relates to formulations and methods for the intranasal and inhalation administration of analgesics having low opioid receptor binding affinity.

BACKGROUND OF THE INVENTION

Pharmacologically active compounds are most commonly administered by the oral route. In particular, analgesics are preferably taken by mouth. However, this convenient route of administration is not always possible for certain patients. Contraindications to oral administration of analgesics can include nausea and/or emesis, oral or gastrointestinal surgery and dysphagia. In addition, rate of analgesia onset is slower and more variable due to first pass effects which compromise the apparent potency of some analgesics and complicate their use. The alternative of administration by injection, e.g., parenteral, intramuscular or subcutaneous injection, is generally not preferred due to patient discomfort and the attendant increased costs associated with the production of and administration of injectable products.

Another, less invasive form of administration is transmucosal administration. Transmucosal administration can be via oral, nasal and/or upper respiratory tract, rectal or vaginal mucosal surfaces, to name the more common non-oral transmucosal routes of administration. Transmucosal administration has the advantage that patients who are unable to swallow can be medicated without recourse to injection. Importantly, transmucosal administration may often provide a more rapid relief of pain, compared to oral administration, by providing direct access to the blood circulation and bypassing the gastrointestinal tract and portal vein circulation and liver metabolism.

A particularly preferred route for transmucosal delivery is intranasal administration for absorption by the nasal mucosal surfaces and/or inhalation for absorption in the bronchial passages of the lungs.

Heretofore, it has been taught that only certain opioid analgesic compounds would be suitable for intranasal transmucosal administration. For example, given the difficulties of delivering compounds across the mucosal barrier and the limited mucosal area that is conveniently available to intranasal administration, only the most potent opioid analgesics, antagonists or mixed agonist/antagonist drugs were taught to be candidates for intranasal delivery. In addition, only those opioid compounds for which oral delivery was variable and problematic were generally considered for intranasal delivery.

For example, U.S. Pat. No. 4,464,378, by Hussain (1984), discloses the intranasal transmucosal administration of certain potent narcotic agonists, antagonists and mixed agonist/antagonists. The Hussain disclosure relates to two classes of compounds, morphine and certain of its structurally close relatives and $\Delta^9$-tetrahydrocannabinol ("delta-9-THC"). The opioid compounds disclosed to be intranasally effective by Hussain are morphine-like compounds retaining a phenolic group, that are also of high potency (typically exhibiting high mu receptor potency, whether agonist, antagonist or mixed agonist/antagonist) and are stated to be rarely used orally because of inefficient and variable absorption by that route. However, Hussain does not teach the intranasal administration of analgesics that are either weak opioids or non-opioid analgesics, which are also well absorbed orally with predictable efficacy.

Wenig et al., U.S. Pat. No. 4,778,810, issued in 1988, discloses the administration of caffeine by nasal administration. Caffeine is a xanthine derivative completely unrelated to the opioids and unrelated to the non-opioid analgesics.

Frost, U.S. Pat. No. 4,880,813, issued in 1989, discloses a method of treatment of allergic rhinitis by the intranasal administration of the narcotic antagonist nalmefene. Nalmefene, (6-methylene-6-desoxy-N-cyclopropylmethyl-14-dihydronomorphine) is a pure opioid antagonist with a prolonged duration of action. Frost states that Nalmefene is believed to act locally on nasal tissues by inhibiting mast cell degranulation provoked by endogenous opioids acting on receptors in the nasal mucosa and the upper respiratory tract. Thus, Frost does not disclose or suggest any systemic delivery of malmefene or any other opioid compound into the blood circulation.

Cohen, U.S. Pat. No. 4,973,596, issued in 1990, discloses a method of intranasally administering the synthetic narcotic analgesic, meperidine, which is a synthetic opioid drug, in a suitable dosage form. However, the effectiveness of intranasal and/or inhalation administration of a weak opioid or non-opioid analgesic is unpredictable from the disclosures of the intranasal effectiveness of morphine or its derivatives, or meperidine, which are conventional strong opioid receptor binding agents. Therefore, the art does not disclose that a weak opioid receptor binding compound, such as the analgesic tramadol, or its derivatives and pharmaceutically acceptable salts, can be delivered by transmucosal and/or inhalation administration.

Tramadol, which has the chemical name (±) trans-2-[(dimethylamino)methyl]-1-(3-methoxyphenyl) cyclohexanol, is an orally active opioid analgesic. Conventional release preparations in the form of capsules, drops, suppositories and formulations for systemic injection, containing tramadol, or more particularly its hydrochloride salt, have been commercially available for many years for use in the treatment of moderate to severe pain (e.g., ZYDOL, by Searle; more recently ULTRAM, by Ortho-McNeil Pharmaceutical). Tramadol hydrochloride is currently administered in single oral doses of 50, 75, 100, 150 and 200 mg to patients with, e.g., postoperative pain. In addition, controlled release preparations for oral administration of tramadol are disclosed by co-owned application, U.S. Ser. No. 08/241,129, filed on May 10, 1994, the disclosure of which is incorporated herein by reference.

Tramadol is a centrally acting synthetic analgesic compound. Unlike conventional opioids, the mechanism of action of tramadol is not completely understood. However, it is known that tramadol binds opioid receptors at low affinity and that the tramadol metabolite mono-O-desmethyltramadol (denoted "M1") binds to opioid receptors at high affinity. The M1 metabolite exhibits substantially greater analgesic activity in animal models than does tramadol. It is also known that tramadol antagonizes reuptake of both norepinephrine and serotonin (in vitro), which may also contribute to the analgesic action of tramadol. In animal models, M1 is up to 6 times more potent than tramadol in producing analgesia and 200 times more potent in opioid receptor binding. However, the contribution to human analgesia of tramadol relative to tramadol metabolite M1 is unknown. The unconventional nature of tramadol-induced antinociception is confirmed by reports that the opioid antagonist naloxone only partially antagonizes tramadol-induced antinociception in animal models. Thus, tramadol exhibits both a unique chemical structure and mechanism of action relative to conventional opioids.

Heretofore there has been no acceptable method or formulation for the transmucosal administration of tramadol, an analgesic which is believed to provide analgesic activity by either or both opioid and non-opioid mechanisms, which is readily absorbed by the oral route and which is not of the highest opioid receptor binding.

OBJECTS OF THE INVENTION

It is accordingly an object of the present invention to provide a pharmaceutical dosage form of an opioid that binds weakly to opioid receptors that can be administered intranasally and/or by inhalation.

Another object of the present invention is to provide a pharmaceutically acceptable dosage form of tramadol that can be administered intranasally and/or by inhalation.

Still another object of the present invention is to provide a method of treating a patient with a pharmaceutically acceptable dosage form of tramadol or its derivatives or pharmaceutically acceptable salts via intranasal and/or inhalation administration.

SUMMARY OF THE INVENTION

In accordance with the above objects and others which will be apparent from the further reading of the specification and of the appended claims, the present invention is related to the surprising discovery that an analgesic that is a weak opioid receptor binding compound can be effectively administered to a warm blooded animal, including a human patient, by administering a pharmaceutically effective amount of the compound, or a pharmaceutically acceptable salt, to the respiratory tract mucosal surfaces of an animal in need of treatment.

The invention also provides for a dosage form for intranasal and/or inhalation administration of a weak opioid or non-opioid analgesic, to a warm blooded animal.

The invention also provides for a method for producing analgesia in a warm blooded animal, such as a human patient, comprising contacting respiratory tract mucosal surfaces, such as the nasal and/or bronchial mucosal surfaces of a warm blooded animal in need of analgesia, with an analgesically effective amount of a weak opioid or non-opioid analgesic.

The compound can be, for example, the weak opioid analgesic tramadol, either as the free base, and/or as its pharmaceutically acceptable derivatives, salts and active metabolites or in any combination thereof. The compound can be administered to the respiratory tract either intranasally and/or by inhalation.

The dosage form can include a pharmaceutically effective amount of a weak opioid or non-opioid analgesic, such as, e.g., tramadol as described above, together with a pharmaceutically acceptable carrier that is suitable for intranasal and/or inhalation administration. The dosage form can contain, for example, tramadol HCl in an amount ranging from 10 mg to 500 mg.

The dosage form suitable for intranasal and/or inhalation administration can be in the form of, e.g., a liquid solution, suspension, emulsion, liposome or similar such multiphasic composition. Preferably, the dosage form includes a carrier of isotonic saline and a pharmaceutically acceptable buffer. For intranasal administration alone, the dosage form may also include an emulsion, a paste, a cream and/or a gel or gauze packing impregnated with the analgesic to be administered. A useful tramadol metabolite, that is also analgesically active, is for example, mono-O-desmethyltramadol, which can also be so administered at an effective dose intranasally and/or by inhalation alone or in combination with another drug, such as, for example, a tramadol and/or a salt or derivative thereof.

DETAILED DESCRIPTION

Accordingly, the present invention provides compositions and methods having utility for the administration, via the respiratory tract, of analgesic drugs having low opioid receptor binding activity. Preferably, the analgesic drugs include the analgesic drug tramadol and derivatives and salts thereof. Reference to "tramadol" herein, unless indicated otherwise, is also understood to encompass all pharmaceutically acceptable forms of tramadol, either as the free base and/or as its pharmaceutically acceptable derivatives, salts and active metabolite and/or combinations thereof, all of which are contemplated to be used in the present compositions and methods. Reference to the term "salt" herein, i.e., tramadol salt, is also intended to encompass the haloacids, i.e., tramadol HCl and the like, unless otherwise indicated.

In accordance with the present invention, an effective amount of a pharmaceutically acceptable form of tramadol is administered intranasally, e.g., by contact with mucosal surfaces in the nasal passages.

Pharmaceutically acceptable carriers for administering tramadol to the nasal mucosal surfaces will be readily appreciated by the ordinary artisan. Such carriers are disclosed, simply by way of example, by Remington's Pharmaceutical Sciences" 16th edition, 1980, Ed. By Arthur Osol, the disclosure of which is incorporated by reference herein in its entirety.

The selection of appropriate carriers depends upon the particular type of administration that is contemplated. For administration via the upper respiratory tract, e.g., the nasal mucosal surfaces, tramadol can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Tramadol containing intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier. The carrier containing the drug can be soaked into a fabric material, such as gauze, that can be applied to the nasal mucosal surfaces to allow for drug penetration therein.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays. For example, tramadol solutions can be administered into the nasal passages by means of a simple dropper (or pipet) that includes a glass, plastic or metal dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

The tear secretions of the eye drain from the orbit into the nasal passages, thus, if desirable, a suitable pharmaceutically acceptable ophthalmic solution can be readily provided by the ordinary artisan as a carrier for the analgesic compounds to be delivered and the analgesic can be administered to the orbit of the eye in the form of eye drops to provide for both ophthalmic and intranasal administration.

In one embodiment, a premeasured unit dosage dispenser that includes a dropper or spray device containing a solution or suspension for delivery as drops or as a spray is prepared containing one or more doses of the drug to be administered. The invention also includes a kit containing one or more unit dehydrated doses of tramadol, together with any required salts and/or buffer agents, preservatives, colorants and the like, ready for preparation of a solution or suspension by the addition of a suitable amount of water. The water may be sterile or nonsterile, although sterile water is generally preferred.

For administration by inhalation into the lower respiratory tract, e.g., the bronchioles, by inhalation, tramadol can be formulated into a solution and/or a suspension of particles in a carrier appropriate for inhalation. Such carriers are also well known to the ordinary artisan familiar with inhalants for the delivery of fine droplets and insufflations for the delivery of inhalable fine particles, on the order of, for example, from about 0.5 to 1 micron, and preferably from about 0.5 to about 0.7 micron, comprised of powders, mists or aerosols, into the respiratory tract (Remington's, Id., at page 1451).

For inhalation of droplets, mists and aerosols various devices such as nebulizers or pressurized aerosol generators are readily available. In addition, such devices can be metered to provide uniformity of dosing (Remington's, Id.).

Dry powder inhalers of types readily disclosed in the art may also be used, as well as micronized shavings of isostatically compressed tablets or discs of drug with or without inert binders such as lactose may be used.

All inhalers may be designed and fashioned to deliver liquid or solid particles to the nasal mucosa as well as the upper and/or lower airways.

In one embodiment, drugs for nasal and/or inhalation administration can be administered as powders. The powdered drug or composition is normally located within a container such as a hard gelatin capsule or a blister package, or a multi-dose devise. The capsule or blister is ruptured or broached within in an inhaler device, thereby enabling the powder to be inhaled. Generally, the mean particle size of the drug used for inhalation is between 1 and 10 micron with the size range between 2 and 5 microns being particularly suitable for penetrating the peripheral airways of the lungs. Such particle size ranges are commonly achieved by micronisation or spray drying.

The finely divided drug powder is often administered as a composition comprising a blend or mixture of the medicament with an inert carrier. Usually the inert carrier has a mean particle size substantially larger than that of the drug. This provides, among other advantages, an improvement in the flow properties and dispensing accuracy of the composition.

Commonly described carrier materials for produced drug, include calcium carbonate and sugars, for example sucrose, mannitol or dextrose or, more particularly, lactose, which are pharmaceutically acceptable and pose no problems of toxicity, since any residues imbibed during dosing are well tolerated upon digestion or may be easily eliminated by disillusion (e.g., in the case of the sugars) or mucocilliary clearance from the lung.

The composition in the capsule or blister is frequently about 25 mgs. This weight probably represents the maximum quantity of powder that may be comfortably inhaled without undue side effects, such as coughing, and also corresponds to the minimum quantity that is usually dispensed by filling machines.

Preferred compositions according to the invention, are those in which the carrier has a particle size distribution in which at least 7% by weight of the carrier particles are at or below about 11 microns, and at least about 20% by weight are at or below about 33 microns, and at least about 20% are at or above 63 microns. Furthermore, particularly those in which the carrier has particle size distribution in which 8% by weight of the carrier particles are at or below 11 microns, and at least 35% by weight are below 33 microns, at least 25% by weight are above 63 microns, especially those in which the carrier has a particle size distribution in which at least 9% by weight are at or below 11 microns, and at least 25% by weight are below 33 microns, and at least 35% by weight are above 63 microns.

Particle sizes referred to in this specification are measured by laser diffraction on a Malvern Instruments Particle Sizer.

Preferred compositions according to the invention for powder inhalation, are those in which the carrier is present at a concentration of about 95.0 to 99.99%. More particularly, from 97.0 to 99.9%, especially from 98.0 to 99.8%, by weight. Processes for preparing such powders, by the application or adaptation of known methods, also constitute features of the invention.

Thus, according to a feature of the invention, a pharmaceutically acceptable solid carrier, preferably in a fluidized bed, is sprayed with a solution of an anti-static additive in a suitable solvent, e.g. ethanol, followed by drying, preferably in a fluidized bed, followed by blending with micro fine solid pharmaceutically active compound or followed by blending with a mixture of a micro fine solid pharmaceutically active compound with a finely divided pharmaceutically acceptable solid carrier.

Anti-static agents suitable for this purpose include those disclosed by Simpkin et al. in International Application WO 94/04133 published March 1994, the disclosure of which is incorporated by reference herein in its entirety.

For powder delivery of analgesic medicament, the medicament, e.g., tramadol, is preferably present in the compositions of the invention at a concentration of about 0.01% to 5.0%. More particularly, from 0.1% to 3.0%, especially from 2.0% by weight.

Insufflation Inhalation Devices

In general, insufflation inhalation devices suitable for use in connection with the particulate dosage forms of the invention comprise a housing having a passageway for the flow of air, in which one end of the passageway is designed for insertion in the mouth or nose, a chamber containing controlled release particles of a cohesive agglomerate of a medicament together with a pharmaceutically acceptable carrier suitable for oral inhalation, wherein the average discrete particle size is from about 0.1 to about 10 microns in diameter for the oro-pulmonary route or 10 to 355 μm for the nasal route, actuating means for releasing a unit dose of said particles into said passageway, such that the unit dose is drawn through said passageway during an inspiration by the patient and is delivered to the naso-pharynx and/or the pulmonary tract of the patient.

The formulations of the present invention may be adapted for use with respect to any oral and/or nasal insufflation device for powdered or solid medicaments. For example, the powder of the present invention may be compressed into a solid dosage form such as a ring tablet which is then placed into an appropriate insufflation device which includes comminuting or other means for providing discrete powder particles in the respirable fraction from the insufflation device when the device is actuated (e.g., when a unit dose of medicament is to administered via inspiration).

There are many devices described in the prior art which are useful for delivering a dose of powdered drug to the respiratory tract or naso-pharynx of a patient. Examples of such devices which would be useful in delivering the formulations of the present invention are described below.

One such device is known as the Bespak device described in International patent application WO 92/00771 (published on Jan. 23, 1992 claiming priority from Great Britain Patent Application No. 9015522.7 filed on Jul. 13, 1990; assigned to Innovata Biomed Limited.), hereby incorporated by reference. The device described therein includes a storage chamber for storing a powdered drug to be administered and a metering member having metering cups in which individual doses of the powdered drug are placed. Air is inhaled through an inhalation passage at one end of the device and directed into contact with the metering cup that has been filled with the powdered drug. The metering cup is oriented upwardly open to face the air stream and to enable the powder to be released from the cup. Upon inhalation, the dose is mixed with the air flow and continues through the mouthpiece to be inhaled.

The metering cups on the metering member are arranged on an outer frusto-conical wall so that each metering cup is position able to be upwardly open and face the air flow during inhalation. The metering member rotates so that the metering cups move between a position in which the cup receives a dose of the powered drug from the storage chamber to a position in which the cup is exposed to the air flow. As one cup is exposed to the air flow, another cup is aligned with the storage chamber and is being filled with powder.

After the dose is blown from the metering cup, and upon subsequent rotation of the metering member, the cup is wiped and cleaned by a wiping element to remove any undispersed powder and then dried via a moisture absorbent material.

Another device for delivery of inhalation powders is described in U.S. Pat. No. 2,587,215 (Priestly), hereby incorporated by reference. Priestly describes an inhaler having a storage chamber containing a powdered medicament, a mixing chamber and means to move a set dose of medicament from the storage chamber to the mixing chamber. The dose is mixed with air in the mixing chamber and inhaled through a mouthpiece.

Yet another inhalation device suitable for delivering powdered inhalation drugs is described in U.S. Pat. No. 4,274,403 (Struve), hereby incorporated by reference. Struve describes an inhaler for administering a powdered drug nasally, which includes storage means for containing a quantity of the drug therein. The storage means includes a feed hole through which the powdered drug may be received from the storage means. The device further includes a dispensing head operatively coupled to the storage means for dispensing the powdered drug more nasally. The dispensing head of the Struve inhaler includes a nozzle, a body portion, a dispensing cylinder and a vent means. The nozzle is shaped to be received in the nasal passage of the user. The nozzle includes a dispensing passageway for dispensing the dose into the nasal cavity of patient.

The body portion is located adjacent the nozzle and has a traverse bore therein. The traverse bore operatively connects the dispensing passageway in the nozzle with the feed hole leading to the drug storage means. The feed hole and the dispensing passageway are transversely offset relative to one another at the points where they enter the transverse bore.

The dispensing cylinder includes a metering chamber. The metering chamber may be selectively aligned with either the feed hole or the dispensing passageway. The dispensing cylinder is slidably received in the transverse bore for movement between a first transverse position in which the metering chamber is aligned with the feed hole and a second transverse position in which the metering chamber is aligned with the dispensing passageway. In its first position, the metering chamber can be filled with a charge of the powdered drug when the inhaler is manipulated. In the second position, places the charge of the powdered drug into the dispensing passageway for inhalation by the user.

The vent means is formed as part of the dispensing cylinder and is capable of venting the metering chamber to atmosphere only in the second position of the cylinder, i.e. when the powder disposed in the device such that it may be inhaled by the user.

Another inhaler device is disclosed in U.S. Pat. No. 4,524,769 (Wetterlin), hereby incorporated by reference. Wetterlin describes a dosage inhaler for administering a micronized pharmacologically active substance to a patient. The inhaler includes a gas conduit means through which gas passes for carrying the micronized substance to be administered. The inhaler further includes a membrane having a plurality of preselected perforated portions, each portion adapted to hold and dispense a reproducible unit dose of less than 50 mg of said active substance, in dry powder form. The powder particles have a particle size of less than 5 micrometers. The membrane is movably connected to the gas conduit means so that one of the preselected portions can be positioned within the gas conduit means so that the substance held in the preselected portion may be dispensed. The remaining preselected portion can be in a position external to said gas conduit means to receive said active substance. The membrane is movable through a plurality of positions whereby each preselected portion of the membrane can be successively positioned within the gas conduit to dispense the unit dose of the active substance held therein. Each preselected portion from which the active substance has been dispensed can be moved to said external position to receive active substance.

GB Patent Application No. 2,041,763, hereby incorporated by reference, describes an inhaler having a powder storage chamber and a rotatable metering member having dosing holes which open to the storage chamber in one position and open to the mixing chamber in another position. Upon rotation of the metering member, the powder is carried from the storage chamber to the mixing chamber to be inhaled.

EP 0 079 478, hereby incorporated by reference, describes an inhaler having a storage chamber, inhalation air passage and rotatable delivery member having a cavity formed therein. The delivery member is rotated from one position in which the cavity receives powder from the storage chamber to another position in which the powder falls from the cavity by the effect of gravity into a collector positioned in the air passage.

U.S. Pat. No. 4,860,740 (Kirk et al.), hereby incorporated by reference, describes an inhaler having a rotatable metering member with recesses formed therein. The recesses contain a powdered medicament. Upon rotation of the metering member, one of the recesses in exposed to the air inhalation passage to be entrained in the air stream and inhaled.

The Easyhaler, described in PCT publication WO 92/09322, hereby incorporated by reference in its entirety, is a device that includes a supply of a pulverized medical substance and a "dosing means", which is a rotatable cylinder having five uniform recesses arranged around the periphery of the cylinder. The cylinder is rotated such that one recess aligns with the supply of drug and is filled by a quantity of the drug while another recess aligns with an air channel connected to the mouthpiece. The filled recess is then rotated to another position in the direct path of an inhalation air flow. The dose is pre-set by the recessed portion of the rotatable dosing means and is flushed clean by the direct air flow through the inhalation chamber.

To operate the device, the rotating dosing means is turned so that a full dosing chamber (having already been filled up after the previous use) is rotated into alignment with the air channel leading to the mouthpiece. Upon inhalation by the user, air is drawn through apertures and nozzles directly into the dosing chamber. The air flow flushes the dosing chamber causing the drug to be carried with the air in the direction of the inhalation through the mouthpiece. The axis of the air channel is arranged at an angle to the axis of the dosing means of between 70° and 110°, but preferably 90° (perpendicular).

U.S. Pat. No. 5,176,132, hereby incorporated by reference, discloses a device for the administration to the lung by inhalation of a medicament in powdered form. The device includes a mouthpiece, a medicament reservoir communicating with said mouthpiece, and metering means for dispensing a dose of medicament from the reservoir. The reservoir contains a compacted body of powdered medicament including an active ingredient having a particle size of from 1 to 10 $\mu$m when in loose powder form. The metering means includes a rotatable helical blade for abrading the compacted body. Thus when actuated, the helical blade abrades the compacted powdered medicament into particles capable of being inhaled into the respiratory tract of a patient.

International patent applications, PCT/EP93/01157 and PCT EP93/01158 (assigned to GGU), hereby incorporated by reference, which are directed to the device and to the ring tablet, respectively.

GGU's device includes an active annular body (medicament reservoir) situated in a mouthpiece. The body forms the beginning of an inhalation tube through which the medicament is inhaled. The drug is in a compacted and annular form. In use, a face mill cutter is caused to rotate, thereby generating particles of the drug. Upon inhalation, air flows through air inlet openings in the casing and in the area of the cutting edges of the face mill cutter. Together with depressions situated between the cutting edges, the inlet openings and the depressions form an air channel leading to the mouthpiece, through which the drug particles are inhaled.

The quantity of each dose is determined by the amount of rotations of the face mill cutter. A spring presses the inhalation tube and thus the drug body toward the face mill cutter. In operation, a wind-up button is rotated to load the spring. By pressing the trigger mechanism, the spring is released thereby rotating the upper portion to which is connected the face mill cutter.

According to International patent application PCT/EP 93/01158, the supply of pharmaceutical agent is present in solid, homogenous tablet form and has an isotropic solid structure. The strength, density and composition of the solid is homogenous. The tablets are made via cold isostatic pressure (CIP) at pressures between 50–500 Megapascal (Mpa).

An effective dose of e.g., intranasal and/or inhaled tramadol is readily determined by the ordinary artisan by titration of the dose until sufficient analgesia is attained or by titrating serum levels of tramadol until serum levels known to be effective are attained. Generally, an effective intranasal and/or inhaled dose of tramadol HCl for an adult is in a range from about 10 to about 500 mg per dose or even from about 50 to about 250 mg per dose. A therapeutically effective serum level of, e.g., tramadol HCl, is reported to range from about 150 to 225 ng/ml of serum. The elimination half-life of tramadol is reported to range from 6 hours in adults to 7 hours in the very elderly (over 75 years). Plasma clearance rates of tramadol have been reported to be 6.4 ml/min/kg in males and 5.7 ml/min/kg in females following a 100 mg IV dose of tramadol. Following a single oral dose, and after adjusting for body weight, females are reported to have a 12% higher peak tramadol concentration and a 35% higher area under the concentration-time curve compared to males. Thus, for example, the artisan will appreciate that the effective dosages will be adjusted in proportion to age, body weight, metabolic activity and renal clearance.

Tramadol HCL is about 30% soluble in water (300 mg/ml). The formulation according to the invention is prepared to include tramadol in a concentration ranging from about 10 to about 300 mg/ml and more, preferably in a concentration ranging from about 150 to about 200 mg per ml. Thus, simply by way of example, the formulations according to the invention can be administered intranasally and/or by inhalation in a volume ranging from about 0.15 ml to about 1 ml or greater, depending on the desired dose. Dosage weights expressed for tramadol hydrochloride can also be readily expressed as equivalent amounts of other tramadol salts, derivatives or active metabolites that may be substituted therefore, in proportion to the relative potency of the other optional forms of tramadol compared to tramadol HCl. Of course, where increased solubility is obtained by supersaturation of the solution, modifications to the structure of tramadol or modifications to the salt or to the solute, the range of concentrations will be increased accordingly.

Derivatives of tramadol may also be used in the present invention. For example, since nasally administered tramadol avoids the direct enterohepatic circulation and the resulting metabolic conversion in the liver, it may be desirable to administer the metabolite mono-O-desmethyltramadol together with or instead of tramadol itself, in order to obtain the benefit of the analgesic activity of this metabolite. In particular, since mono-O-desmethyltramadol is about 6 times more potent than tramadol as an analgesic, the effective dose will be adjusted accordingly. Dosages of other tramadol salts or derivatives should be adjusted accordingly in proportion to potency relative to tramadol HCl.

The following examples, which are in no way intended to limit the scope of the present invention, illustrate the preparation of typical compositions and unit dosage forms suitable for nasal administration of tramadol.

EXAMPLE 1

Intranasal Tramadol Formulation I

A formulation of tramadol and a viscous carrier is prepared by art known methods from the ingredients of Formula I and Formula II.

| Formula I | |
|---|---|
| Tramadol HCl | 20 g |
| Methyl Cellulose | 300 mg |
| Tween 80 | 30 mg |
| Purified Water | 100 ml |
| Formula II | |
| Tramadol HCl | 20 g |
| Methyl Cellulose | 1 mg |
| Tween 80 | 50 mg |
| Glycerin | 5 ml |
| Purified Water | 100 ml |

The formulations are prepared by dissolving the tramadol HCl in water or buffered isotonic saline. While stirring methyl cellulose and then Tween 80 is added. Optionally, viscosity enhancers, colorants and fragrances are also added.

EXAMPLE 2

Intranasal Administration of Formula 1

Formula I of Example 1 is prepared according to art known procedures, buffered to a suitable pH ranging from about pH 6.0 to about 6.5 so that the formulation includes tramadol HCl at a concentration of about 200 mg per ml. About 1 ml of the formulation is placed into a unit dosage form nasal dropper or intranasal spray bottle. The drops or spray are conventionally administered to the nasal passages of a patient in need of analgesia for postoperative oral surgery. The patient experiences rapid relief from postoperative pain.

EXAMPLE 3

Intranasal Administration of Formula 2

Formula II of Example 1 is prepared according to art known procedures as described by Example 2 and is placed into a nasal dropper or intranasal spray bottle. The addition of glycerin to the formulation provides additional viscosity and moisturizing properties for greater patient comfort and ease of delivery. About 1 ml of the formulation is placed into a unit dosage form nasal dropper or intranasal spray bottle. The drops or spray are conventionally administered to the nasal passages of a patient in need of analgesia for postoperative oral surgery. The patient experiences rapid relief from postoperative pain.

A formulation of tramadol and an inhalation carrier is prepared by art known methods (e.g., WO 94/04133) from the ingredients of Formulas III and V.

EXAMPLE 4

Powderous Inhalation Formulation of Tramadol

|  | Weight Percent |
|---|---|
| Formula III | |
| Aerosol Grade Lactose | 78.8 |
| Sorbitan Triocate (Span 85) | 0.4 |
| Tramadol HCl | 1.0 |
| Fine Grade Lactose | 19.8 |
| Formula IV | |
| Aerosol Grade Lactose | 79.0 |
| Sorbitan Triocate (Span 85) | 0.2 |
| Tramadol HCl | 1.0 |
| Fine Grade Lactose | 19.8 |
| Formula V | |
| Aerosol Grade Lactose | 79.0 |
| Sorbitan Triocate (Span 85) | 0.0 |
| Tramadol HCl | 1.0 |
| Fine Grade Lactose | 19.8 |

Formulas III and IV are prepared by spraying a solution of Span 85 (acid starter agent) in industrial methylated spirits onto the aerosol grade lactose, followed by drying, in a fluid bed coater/drier, to give a coated, free-flowing powder. The tramadol HCl and fine grade lactose are then blended with the coated lactose.

Formula V is prepared by blending the lactose and tramadol HCl. The aerosol grade lactose has a size distribution, determined by known methods by laser diffraction, of 1.7% less than or equal to 11 microns, 6.4% less than or equal to 33 microns, and 63.7% more than or equal to 63 microns, by weight, with a median size of 70.8 microns.

The fine grade lactose used has a size distribution, determined by known methods by laser diffraction, of 30% less than or equal to 11 microns, 85% less than or equal to 33 microns, and 0.2% more than or equal to 63 microns, by weight, with a median size of 18 microns.

Conclusion

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:

1. An intranasal tramadol formulation comprising an active agent consisting essentially of tramadol in a form selected from the group consisting of tramadol free base, pharmaceutically acceptable salts thereof and any combinations thereof; said tramadol being dispersed within a pharmaceutically acceptable carrier for intranasal administration; said formulation being contained in a pharmaceutically acceptable dispenser for intranasal administration which dispenses an amount of said formulation to the mucousal surfaces in the nasal passages of a mammal to provide intranasal absorption of an analgesically effective amount of said tramadol.

2. The intranasal tramadol formulation according to claim 1, wherein said tramadol is in the form of the hydrochloride salt.

3. The intranasal tramadol formulation according to claim 1, wherein said pharmaceutically acceptable carrier is selected from the group consisting of a liquid solution, a suspension, an emulsion, a liposome, a paste, a cream and a gel.

4. The intranasal tramadol formulation according to claim 1, wherein said pharmaceutically acceptable carrier comprises isotonic saline solution or suspension.

5. The intranasal tramadol formulation according to claim 1, wherein said pharmaceutically acceptable carrier has a pH ranging from 4.0 to about pH 7.4.

6. The intranasal tramadol formulation according to claim 5, wherein said tramadol is present in an amount ranging from about 10 mg to about 300 mg per ml.

7. The intranasal tramadol formulation according to claim 1, wherein said dispenser administers drops.

8. The intranasal tramadol formulation according to claim 1, wherein said dispenser administers a spray.

9. The intranasal tramadol formulation according to claim 1, wherein said dispenser is a simple dropper.

10. The intranasal tramadol formulation according to claim 1, wherein said dispenser is a manually powered intranasal pump dispenser.

11. The intranasal tramadol formulation according to claim 1, wherein said dispenser is an electrically powered intranasal pump dispenser.

12. The intranasal tramadol formulation according to claim 1, wherein said dispenser is a squeeze bottle.

* * * * *